(12) United States Patent
Maignan et al.

(10) Patent No.: US 6,514,507 B2
(45) Date of Patent: Feb. 4, 2003

(54) HYDROXYDECENOIC ACID COMPOUNDS FOR PROMOTING DESQUAMATION/ EPIDERMAL RENEWAL OF THE SKIN AND/ OR COMBATING SKIN AGING

(75) Inventors: Jean Maignan, Tremblay (FR); Sylvie Genard, Paris (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/996,904

(22) Filed: Nov. 30, 2001

(65) Prior Publication Data

US 2002/0086041 A1 Jul. 4, 2002

Related U.S. Application Data

(62) Division of application No. 09/399,181, filed on Sep. 20, 1999.

(30) Foreign Application Priority Data

Sep. 22, 1998 (FR) .............................. 98 11811

(51) Int. Cl.[7] .............................. A61K 6/00; A61K 7/00; A61K 31/74; A61K 31/20; A01N 37/00
(52) U.S. Cl. .................. 424/401; 424/78.03; 514/558; 514/560
(58) Field of Search .............................. 424/401, 78.03; 514/558, 560

(56) References Cited

U.S. PATENT DOCUMENTS

| 5,399,353 | A | * | 3/1995 | Bartnik et al. .............. 424/438 |
| 5,476,661 | A | | 12/1995 | Pillai et al. |
| 5,708,028 | A | * | 1/1998 | Degwert et al. ............ 514/560 |
| 5,747,051 | A | | 5/1998 | Granger et al. |
| 6,036,966 | A | * | 3/2000 | Youssefych .................. 424/401 |
| 6,124,364 | A | | 9/2000 | Breton et al. |

FOREIGN PATENT DOCUMENTS

| FR | 2684988 | | 6/1993 |
| JP | 61176510 | * | 8/1986 |
| JP | 2684988 | * | 6/1998 |
| JP | 10147514 | | 6/1998 |
| JP | 8(1996)323492 | * | 6/1998 |

OTHER PUBLICATIONS

Patent Abstracts of Japan, vol. 10, No. 383, Dec. 23, 1986 & JP 61 176510A, Aug. 8, 1986.
Patent Abstracts of Japan, vol. 98, No. 11, Sep. 30, 1998 & JP 10 147514, Jun. 2, 1998.
Chemical Abstracts, vol. 125, No. 3, Jul. 15, 1996, Abstract No. 31721q.

* cited by examiner

Primary Examiner—Dameron L. Jones
Assistant Examiner—Lauren Q. Wells
(74) Attorney, Agent, or Firm—Burns, Doane, Swecker & Mathis, L.L.P.

(57) ABSTRACT

10-Hydroxy-2-decenoic acid and derivatives thereof are well suited for promoting desquamation and/or stimulating epidermal renewal and/or combating intrinsic/extrinsic aging of the skin of a candidate individual in need of such treatment, by administering thereto, for such period of time as required to elicit the desired response, an effective amount of at least one of said 10-hydroxy-2-decenoic acid or derivative thereof.

23 Claims, 1 Drawing Sheet

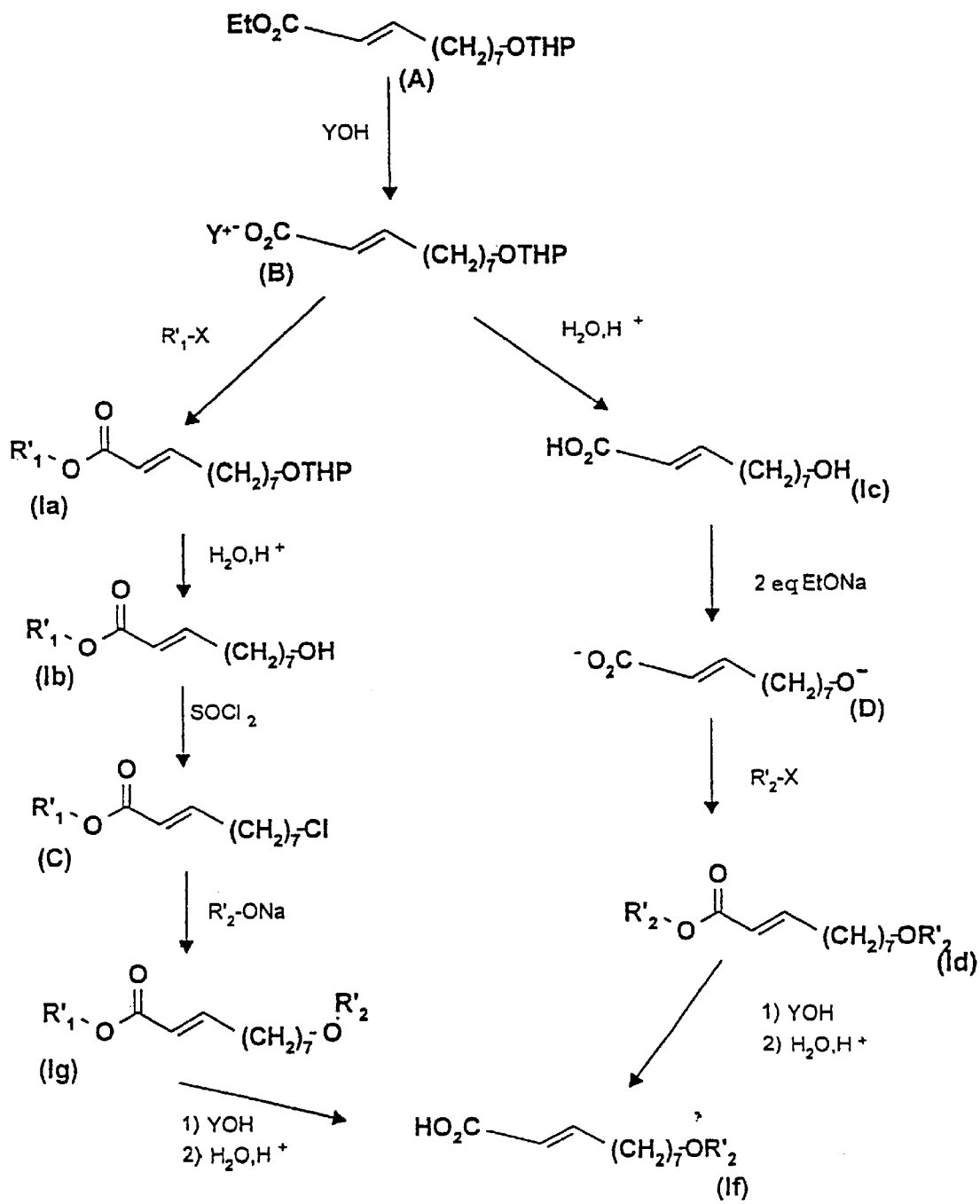
Figure I

HYDROXYDECENOIC ACID COMPOUNDS FOR PROMOTING DESQUAMATION/ EPIDERMAL RENEWAL OF THE SKIN AND/ OR COMBATING SKIN AGING

CROSS-REFERENCE TO PRIORITY APPLICATION

This application claims priority under 35 U.S.C. §119 of FR-98/11811, filed Sep. 22, 1998, hereby expressly incorporated by reference.

This application is a divisional of application Ser. No. 09/399,181, filed on Sep. 20, 1999.

BACKGROUND OF THE INVENTION

1. Technical Field of the Invention

The present invention relates to novel 10-hydroxy-2-decenoic acid compounds and to the use of an effective amount of 10-hydroxy-2-decenoic acid or of at least one derivative thereof for promoting desquamation of the skin and/or to stimulate epidermal renewal and/or to combat aging of the skin.

This invention also relates to hydroxydecenoic compositions for promoting desquamation of the skin and/or for stimulating epidermal renewal and therefore for combating intrinsic and/or extrinsic cutaneous aging, as well as to a nontherapeutic regime/regimen for promoting desquamation and/or to combat aging of the skin.

2. Description of the Prior Art

Desquamation is a natural phenomenon associated with the fact that the epidermis, which constitutes the upper layer of the skin, is in constant regeneration. The epidermis is composed of several layers of cells, the deepest of which is the basal layer consisting of undifferentiated cells. Over time, these cells differentiate and migrate to the surface of the epidermis, constituting the various layers thereof, until they form at the surface of the epidermis the corneocytes, which are dead cells which are eliminated by desquamation. This loss of surface is compensated for by the migration of cells from the basal layer towards the surface of the epidermis. This amounts to perpetual renewal of the skin. Forced elimination of the horny layer accelerates renewal and makes it possible to combat aging.

At the same time, these cells continue their differentiation, the final stage of which is the corneocyte. These are dead cells which constitute the final layer of the epidermis, namely, the outermost layer, also known as the stratum corneum.

Cutaneous skin aging resulting from intrinsic or extrinsic factors is reflected by the appearance of wrinkles and fine lines, by yellowing of the skin, which develops a parchment-like appearance accompanied by the development of pigmentary blemishes, by the disorganization of the elastin and collagen fibers, causing a loss of elasticity, flexibility and firmness, or by the appearance of telangiectases.

Certain of these signs of aging are more particularly associated with intrinsic or physiological aging, namely, with "normal" aging due to age or chronobiological aging, whereas others are more specific to extrinsic aging, namely, aging caused in general by the environment; this relates more particularly to photoaging due to exposure to the sun, to light or to any other radiation.

The present invention relates to not only intrinsic or physiological aging, but also to extrinsic aging.

The changes in the skin due to intrinsic aging are the consequence of a genetically programmed senescence involving endogenous factors. This intrinsic aging causes, in particular, a slowing down of the renewal of the cells of the skin, which is reflected essentially by the appearance of detrimental clinical changes, such as a reduction in the subcutaneous adipose tissue and the appearance of small wrinkles or fine lines, and by histopathological changes, such as an increase in the number and thickness of elastic fibers, a loss of vertical fibers from the membrane of the elastic tissue, and the presence of large irregular fibroblasts in the cells of this elastic tissue.

In contrast, extrinsic aging causes detrimental clinical changes, such as large wrinkles and the formation of a flaccid and weathered skin, and histopathological changes, such as an excessive accumulation of elastic material in the epidermis and degeneration of the collagen fibers.

Various active agents for combating cutaneous aging are known to this art.

Thus, U.S. Pat. No. 4,603,146 describes the use of retinoic acid and derivatives thereof in cosmetic compositions for combating cutaneous aging.

Moreover, numerous patents and publications (see, for example, EP-A-413,528) describe and many commercially available cosmetic compositions include α-hydroxy acids, such as lactic acid, glycolic acid or citric acid, for treating/combating cutaneous aging.

Too, the β-hydroxy acids, and more especially salicylic acid and derivatives thereof, are known for their desquamating properties (see WO-A-93/10756 and U.S. Pat. No. 4,767,750).

All of the aforesaid prior art compounds elicit action against aging of the skin by promoting desquamation, namely, the removal of the "dead" cells located at the surface of the horny layer of the epidermis. This "desquamating" property is also referred to, often incorrectly, as a keratolytic property.

However, the prior art compounds also present objectionable side effects, such as stinging, pricking, stabbing pains and sensations of heat and redness which are unpleasant for the user.

Need therefore continues to exist for antiaging agents having an action which is at least as effective as that of the compounds of the prior art, but which do not present the disadvantages thereof.

SUMMARY OF THE INVENTION

Accordingly, a major object of the present invention is the provision of novel compounds and active agents which promote desquamation of the skin and/or which stimulate epidermal renewal, while at the same time avoiding the stinging, pricking, stabbing pains or sensations of heat or redness which are unpleasant for the user and which to date have characterized the state of this art.

10-Hydroxy-2-decenoic acid is present in the trans form in royal jelly, constituting approximately 10% of the dry mass thereof and from which it was extracted for the first time in 1940 by Townsend and Lucas (*Biochem. J.*, 34, 1155 (1940)).

10-Hydroxy-2-decenoic acid in the trans form is implicated in the differentiation of the female castes in bees.

In the prior art, this acid has been formulated into compositions for the prevention of leukemias, depigmentary compositions, compositions having activity with regard to the loss and regrowth of hairs and heads of hair, antiseborrhoeic compositions, antitumoral compositions or bacteriostatic compositions.

Heretofore, however, it had not been recognized that 10-hydroxy-2-decenoic acid or any derivative thereof could be administered for promoting desquamation of the skin and/or stimulating epidermal renewal and therefore combating intrinsic and/or extrinsic cutaneous aging.

Thus, it has now unexpectedly and surprisingly been determined that administering an effective amount of 10-hydroxy-2-decenoic acid or of at least one particular derivative thereof promotes desquamation of the skin and/or stimulates epidermal renewal and, hence, is useful for combating skin aging.

BRIEF DESCRIPTION OF THE DRAWING

The FIGURE of Drawing sets forth reaction schemes/mechanisms illustrating representative syntheses for the preparation of the hydroxydecenoic acid compounds according to the present invention.

DETAILED DESCRIPTION OF BEST MODE AND SPECIFIC/PREFERRED EMBODIMENTS OF THE INVENTION

More particularly according to the present invention, desquamation of the skin is promoted and/or epidermal renewal is stimulated, and thus cutaneous skin aging is combated, by topically applying thereto, for such period of time as required to elicit the desired response, an effective amount of at least one compound having the structural formula (I):

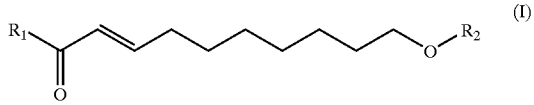

in which $R_1$ is a radical or an atom selected from among a hydrogen atom; an —NR'R" radical, wherein R' and R", which may be identical or different, are each a hydrogen atom, a $C_1$–$C_4$ alkyl radical, a $C_3$–$C_4$ alkenyl radical or cyclopentyl radical or cyclohexyl radical, with the proviso that R' and R" may together form a heterocycle with the nitrogen atom from which they depend, and with the further proviso that the —NR'R" radical may be the residue of an amino acid or glucosamine; an —$OR_3$ radical, wherein $R_3$ is a radical or an atom selected from from a hydrogen atom, a linear or branched $C_1$ to $C_{18}$ alkyl radical, a linear or branched $C_2$ to $C_{18}$ alkenyl radical, or a linear or branched $C_1$ to $C_{18}$ perfluoroalkyl radical, with the proviso that the alkyl or alkenyl radicals may be substituted by one or more hydroxyl and/or amino and/or aminoalkyl groups, and with the further proviso that these radicals can additionally be substituted by a carboxylic acid functional group, or a linear or branched $C_1$–$C_{18}$ alkyl carboxylate functional group; an aryl radical or an aralkyl radical optionally substituted by linear or branched $C_1$–$C_{18}$ alkyl radicals, by —CO—R''' acyl radicals or by —OR''' alkoxy radicals, wherein R''' is a hydrogen atom, or a hydroxyl radical, or a linear or branched $C_1$–$C_1$ alkyl radical; $R_2$ is a radical or an atom selected from among a hydrogen atom, a linear or branched $C_1$ to $C_{18}$ alkyl radical, a linear or branched $C_2$ to $C_{18}$ alkenyl radical, a linear or branched $C_1$ to $C_{18}$ perfluoroalkyl radical, a $C_1$–$C_{18}$ mono- or polyhydroxyalkyl radical, a cyclopentyl or cyclohexyl radical, a tetrahydropyranyl radical, a radical having the following formula (II):

in which $R_4$ is a linear or branched $C_1$–$C_{18}$ alkyl radical, a $C_1$–$C_8$ monohydroxyalkyl radical, a $C_3$–$C_6$ polyhydroxyalkyl radical having from 2 to 5 hydroxyl groups, an —NR'R" radical, wherein R' and R", which may be identical or different, are each a hydrogen atom, or a $C_1$–$C_4$ alkyl radical, or a $C_3$–$C_4$ alkenyl radical, or a cyclopentyl radical or a cyclohexyl radical, with the proviso that R' and R" may together form a heterocycle with the nitrogen atom from which they depend, and with the further proviso that the —NR'R" radical may be the residue of an amino acid or glucosamine; an aralkyl radical or an aryl radical optionally substituted by one or more linear or branched $C_1$–$C_{18}$ alkyl radicals, or by a —CO—R''' acyl radical, or by an —OR''' alkoxy radical, wherein R''' is as defined above; and the corresponding salts, isomers and stereoisomers thereof; with the proviso that, if $R_2$ is a hydrogen atom, then $R_3$ cannot be an N,N-dimethylaminoethyl group or a radical of the formula:

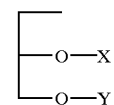

in which X and Y, which are identical, are each a hydrogen atom or a radical:

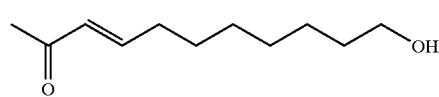

or in which X is a hydrogen atom and Y is a radical:

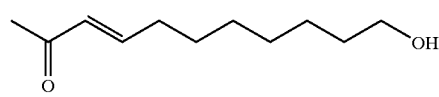

or in which X is a radical:

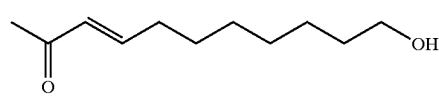

and Y is:

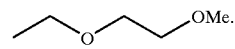

The salts of the compounds which are administered according to the invention are selected, in particular, from among alkali metal or alkaline earth metal salts, or zinc, magnesium or strontium salts, the salts of an organic amine, or quaternary ammonium salts, when they comprise at least one free acid functional group.

The salts of the compounds according to the invention are selected, in particular, from the salts of an inorganic or organic acid, in particular hydrochlorides, hydrobromides or citrates, when they comprise at least one amine functional group.

In a preferred embodiment of the invention, a compound of formula (I) is administered in which $R_1$ is an —NR'R" group, wherein R' is a hydrogen atom and R" is a $C_1$–$C_6$ mono- or polyhydroxyalkyl group.

In another preferred embodiment of the invention, a compound of formula (I) is administered in which $R_1$ represents the —$OR_3$ radical, wherein $R_3$ is a hydrogen atom, an ethyl group, a carboxymethyl group, a 1'-carboxyethyl group or a 1'-carboxyoctyl group, or, alternatively, a 2'-carboxyphenyl group or a 2'-carboxy-4'-octanoylphenyl group.

In yet another preferred embodiment of the invention, a compound of formula (I) is administered in which $R_2$ is a hydrogen atom, a 2'-hydroxyethyl group, a 2',3'-dihydroxypropyl group, a 2'-hydroxy-propyl group, or a —CO—$R_4$ group, wherein $R_4$ is a hydroxymethyl group, a 1'-hydroxyethyl group, a 1'-hydroxyheptyl group, a 2'-hydroxyphenyl group, or a 2'-hydroxy-4'-octanoylphenyl group.

The preferred compounds according to the invention are those in which:

when $R_1$ is the —OH radical, then $R_2$ is a hydrogen atom, a 2'-hydroxyethyl group, a 2',3'-dihydroxypropyl group or a 2'-hydroxypropyl group;

when $R_2$ is a hydrogen atom, then $R_1$ is an —NR'R" group, wherein R' is a hydrogen atom and R" is a $C_1$–$C_6$ mono- or polyhydroxyalkyl group;

when $R_2$ is a hydrogen atom, then $R_1$ is the —$OR_3$ radical, wherein $R_3$ is a carboxymethyl group, a 1'-carboxyethyl group, a 1'-carboxyheptyl group, a 2'-carboxyphenyl group, or a 2'-carboxy-4'-octanoylphenyl group;

when $R_2$ is the —CO—$R_4$ group, then $R_4$ is a hydroxymethyl group, a 1'-hydroxyethyl group, a 1'-hydroxyheptyl group, a 2'-hydroxyphenyl group or a 2'-hydroxy-4'-octanoylphenyl group.

The compounds of formula (I) according to the invention can be of natural or synthetic origin. By the term "natural origin" is intended a compound extracted from natural material in which it is present. By the term "synthetic origin" is intended a compound prepared by chemical synthesis or by biotechnology.

Of course, the compounds of formula (I) can be utilized either alone or in admixture.

Likewise according to the invention, the compounds of the invention can be administered in their cis or trans form.

The amount of the compounds of formula (I) which are administered according to the invention very obviously depends on the desired effect and must be an amount which is effective in promoting desquamation of the skin and/or stimulating epidermal renewal and thus combating intrinsic and/or extrinsic cutaneous aging.

For example, the amount of compound of formula (I) administered according to the invention advantageously ranges from 0.001% to 20% and preferably from 0.01% to 5% by weight of the total weight of the composition.

This invention also features compositions for promoting desquamation of the skin and/or stimulating epidermal renewal and thus combating intrinsic and/or extrinsic cutaneous aging which comprises at least one compound of formula (I).

In yet another embodiment of the invention, a nontherapeutic regime/regimen is provided for promoting desquamation of the skin and/or stimulating epidermal renewal and thus combating intrinsic and/or extrinsic cutaneous aging, wherein a cosmetic composition comprising a compound of formula (I) is topically applied onto the skin.

The present invention also features novel derivatives of 10-hydroxy-2-decenoic acid having the structural formula (I'):

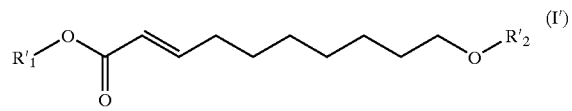

in which $R'_1$ is a radical selected from among a hydrogen atom, a radical of the formula:

a radical of the formula:

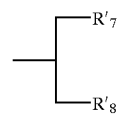

or a radical of the formula:

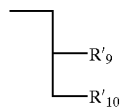

wherein $R'_5$, $R'_6$, $R'_7$, $R'_8$, $R'_9$ and $R'_{10}$ are as defined below; $R'_2$ is a radical or an atom selected from among a hydrogen atom, a radical of the formula:

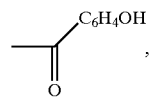

a radical of the formula:

a radical of the formula:

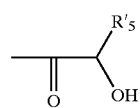

wherein $R'_5$ is a hydrogen atom, a —$CH_3$ radical or a —$C_6H_{13}$ radical, $R'_6$ is a —COOH radical, a —$CO_2$—$CH_2$—$CH_3$ radical, or, alternatively, a —$CH_2OH$ radical or a hydroxyl radical, $R'_7$ is an —OH radical, a radical of the formula:

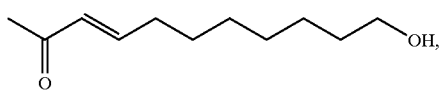

or a radical of the formula:

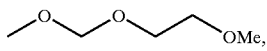

R'$_8$ is an —OH radical or a radical of the formula:

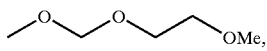

R'$_9$ is a radical of the formula:

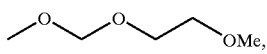

R'$_{10}$ is a radical of the formula:

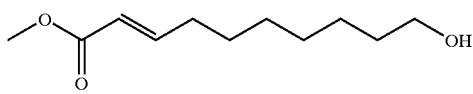

or a radical of the formula:

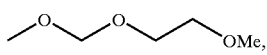

with the proviso that, when R'$_1$ is a hydrogen atom, then R'$_2$ cannot be a hydrogen atom, and that, when R'$_7$ is a radical of the formula:

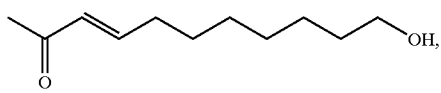

then R'$_8$ cannot be a radical of the formula:

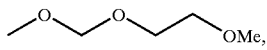

and the corresponding salts, isomers and stereoisomers thereof.

The salts of the compounds in accordance with the invention are selected in particular from among the alkali metal or alkaline earth metal salts, or from zinc, magnesium or strontium salts, the salts of an organic amine or quaternary ammonium salts, when they comprise at least one free acid functional group.

The salts of the compounds in accordance with the invention are selected, in particular, from among the salts of an inorganic or organic acid, in particular hydrochlorides hydrobromides or citrates, when they comprise at least one amine functional group.

This invention thus features compositions which comprise at least one of the compounds having the above formula (I').

Of course, the compositions according to the invention can comprise the compounds of formula (I') alone or as mixtures in all proportions.

The amount of the compounds of formula (I') present in the compositions of the invention is, of course, a function of the desired effect and can thus vary to a great extent.

To provide an order of magnitude, the composition can comprise at least one compound of formula (I) in an amount constituting from 0.001% to 20% by weight of the total weight of the composition and preferably in an amount constituting from 0.01% to 5% by weight of the total weight of the composition.

The compositions of the invention can be ingested, injected or topically applied to the skin (over any cutaneous region of the body), hair, nails or mucous membranes (buccal, jugal, gingival, genital or connective). Depending on the mode of administration, the compositions according to the invention can be provided in all of the pharmaceutical dosage forms conventional to this art.

For topical application onto the skin, the compositions can be formulated, in particular, as an aqueous or oily solution, or as a dispersion of the lotion or serum type, as emulsions with a liquid or semi-liquid consistency of the milk type, obtained by dispersion of a fatty phase in an aqueous phase (O/W) or vice versa (W/O), or as suspensions or emulsions with a soft consistency of the aqueous or anhydrous gel or cream type, or alternatively as microcapsules or microparticles, or as vesicular dispersions of ionic and/or nonionic type. These compositions are formulated via the usual techniques.

The subject compositions can also be used for the hair in the form of aqueous, alcoholic or aqueous/alcoholic solutions or in the form of creams, gels, emulsions or foams or, alternatively, in the form of aerosol compositions also comprising a pressurized propellant.

The compositions according to the invention can also be a hair care composition and in particular a shampoo, a hair setting lotion, a treating lotion, a styling cream or gel, a dyeing composition (in particular oxidation dyeing composition), optionally in the form of coloring shampoos, hair restructuring lotions, a permanent wave composition (in particular a composition for the first step of permanent waving), a lotion or gel for combating hair loss, an antiparasitic shampoo, and the like.

For injection, the compositions can be provided in the form of an aqueous or oily lotion or in the form of a serum. For administration to the eyes, same can be formulated as eyedrops and, for ingestion, they can be provided in the form of capsules, granules, syrups or tablets.

The amounts of the various constituents of the compositions according to the invention are those conventionally used in the fields under consideration.

The compositions according to the invention can also be solid preparations constituting cleansing soaps or bars.

The subject compositions can also be packaged in the form of an aerosol composition also comprising a pressurized propellant.

When the composition is an emulsion, the proportion of the fatty phase advantageously ranges from 5% to 80% by weight and preferably from 5% to 50% by weight with respect to the total weight of the composition. The oils, waxes, emulsifiers and coemulsifiers incorporated in the composition in the form of an emulsion are selected from among those conventionally used in the cosmetics field. The emulsifier and the coemulsifier are typically present in the composition in a proportion ranging from 0.3% to 30% by weight and preferably from 0.5% to 20% by weight with respect to the total weight of the composition. In addition, the emulsion can comprise lipid vesicles.

When the composition is an oily solution or gel, the fatty phase can constitute more than 90% of the total weight of the composition.

The compositions of the invention are well suited for cosmetic or pharmaceutical applications. The compositions of the invention are preferably cosmetic compositions.

In known manner, the subject cosmetic compositions can also comprise additives and adjuvants usual in the cosmetics field, such as hydrophilic or lipophilic gelling agents, hydrophilic or lipophilic additives, preservatives, antioxidizing agents, solvents, fragrances, fillers, UV-screening agents, odor absorbers and colorants. The amounts of these various additives and adjuvants are those conventionally formulated in the cosmetics field and, for example, range from 0.01% to 10% by weight of the total weight of the composition. These additives and adjuvants, depending on their nature, can be introduced into the fatty phase, into the aqueous phase and/or into the lipid spherules.

Exemplary oils or waxes according to the invention include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoro-polyethers), beeswax, carnauba wax or paraffin wax. Fatty alcohols and fatty acids (stearic acid) can be added to these oils.

Exemplary emulsifiers according to the invention include, for example, glycerol stearate, polysorbate 60 and the PEG-6/PEG-32/Glycol Stearate mixture marketed under the trademark Tefose® 63 by Gattefosse.

Exemplary solvents according to the invention include the lower alcohols, in particular ethanol and isopropanol, or propylene glycol.

And exemplary hydrophilic gelling agents according to the invention include carboxyvinyl polymers (carbomer), acrylic copolymers, such as acrylate/alkyl acrylate copolymers, polyacrylamides, polysaccharides, such as hydroxypropylcellulose, natural gums and clays and exemplary lipophilic gelling agents include modified clays, such as bentones, metal salts of fatty acids, such as aluminum stearates, and hydrophobic silica, ethylcellulose or polyethylene.

The subject compositions can contain other hydrophilic active principles, such as proteins or protein hydrolysates, amino acids, polyols, urea, allantoin, sugars and sugar derivatives, water-soluble vitamins, plant extracts and hydroxy acids.

Exemplary lipophilic active agents include retinol (vitamin A) and derivatives thereof, tocopherol (vitamin E) and derivatives thereof, essential fatty acids, ceramides, essential oils, or salicylic acid and derivatives thereof.

According to this invention, the composition can combine at least one compound of formula (I) with other active agents. Exemplary such active agents include:

(1) agents which improve the activity with respect to hair regrowth and/or with respect to slowing down hair loss and which are already known for such activity, such as, for example, nicotinic acid esters, including in particular tocopherol nicotinate, benzyl nicotinate and nicotinates of $C_1$–$C_6$ alkyls, such as methyl or hexyl nicotinates, pyrimidine derivatives, such as 2,4-diamino-6-piperidinopyrimidine 3-oxide or "Minoxidil", described in U.S. Pat. Nos. 4,139,619 and 4,596,812, or agents which promote hair regrowth, such as those described in the European patent application assigned to the assignee hereof, published under the number 0,648,488;

(2) agents which modify cutaneous pigmentation and/or proliferation and/or differentiation, such as retinoic acid and isomers thereof, retinol and esters thereof, vitamin D and derivatives thereof, estrogens, such as estradiol, kojic acid or hydroquinone;

(3) antibacterials, such as clindamycin phosphate, erythromycin or antibiotics of the tetracycline class;

(4) agents for combating parasites, in particular metronidazole, crotamiton or pyrethroids;

(5) antifungals, in particular compounds belonging to the imidazole class, such as econazole, ketoconazole or miconazole or salts thereof, polyene compounds, such as amphotericin B, compounds of the allylamine family, such as terbinafine, or alternatively octopirox;

(6) antiviral agents, such as acyclovir;

(7) steroidal anti-inflammatory agents, such as hydrocortisone, betamethasone valerate or clobetasol propionate, or nonsteroidal anti-inflammatory agents, such as, for example, ibuprofen and salts thereof, diclofenac and salts thereof, acetylsalicylic acid, acetaminophen or glycyrrhizic acid;

(8) anaesthetic agents, such as lidocaine hydrochloride and derivatives thereof;

(9) antipruritic agents, such as thenaldine, trimeprazine or cyproheptadine;

(10) keratolytic agents, such as α- and β-hydroxycarboxylic acids or β-ketocarboxylic acids, their salts, amides or esters and more particularly hydroxy acids, such as glycolic acid, lactic acid, salicylic acid, citric acid and generally fruit acids, and 5-(n-octanoyl)salicylic acid;

(11) agents for combating free radicals, such as α-tocopherol or esters thereof, superoxide dismutases, certain metal chelating agents or ascorbic acid and esters thereof;

(12) antiseborrhoeics, such as progesterone;

(13) antidandruff agents, such as octopirox or zinc pyrithione;

(14) antiacne agents, such as retinoic acid or benzoyl peroxide;

(15) extracts of plant, marine or bacterial origin.

Other compounds can also be added to the above, namely, for example, diazoxide, spiroxazone, phospholipids, such as lecithin, linoleic and linolenic acids, salicylic acid and derivatives thereof described in FR-2,581,542, such as salicylic acid derivatives substituted by an alkanoyl group having from 2 to 12 carbon atoms in the 5-position of the benzene ring, hydroxycarboxylic or ketocarboxylic acids and esters thereof, lactones and their corresponding salts, anthralin, carotenoids, eicosatetraenoic and eicosatrienoic acids or their esters and amides, vitamin D and derivatives thereof, or extracts of plant or bacterial origin.

Thus, in a preferred embodiment, the compositions according to the invention also comprise at least one agent selected from among antibacterial agents, agents for combating parasites, antifungals, antivirals, anti-inflammatories, antipruritics, anaesthetics, keratolytics, agents for combating free radicals, antiseborrhoeics, antidandruff agents, antiacne agents and/or agents which decrease cutaneous pigmentation and/or proliferation and/or differentiation, or extracts of plant, marine or bacterial origin.

The pharmaceutical compositions according to the invention are conveniently administered parenterally, enterally or topically. Such pharmaceutical compositions are preferably administered topically.

The compounds of the invention can be synthesized via conventional processes, usual in organic syntheses.

The synthetic routes which can be used according to the invention are summarized in FIG. I.

The compounds of the invention are prepared from ethyl 10-[(tetrahydro-2H-pyran-2-yl)oxy]-2-decenoate of formula (A, FIGURE (1)), the preparation of which is described in the literature (Matsui S., *Bull. Chem. Soc. Jpn.*, 1984, 57 (2), 426-34 and Vig O., Vig A., Mann J. and Gupta K., *J. Indian Chem. Soc.*, 1975, 52 (6), 538-40, for example).

This ester is converted into a salt of 10-[(tetrahydro-2H-pyran-2-yl)oxy]-2-decenoic acid (formula B, FIGURE (1)) by saponification at a temperature of from 20° C. to 60° C. using one equivalent or an excess (2 or 3 equivalents) of an inorganic base, such as sodium hydroxide or potassium hydroxide (YOH, Y=Na or K), stirred in ethanol or in an aprotic solvent, such as dimethylformamide or dimethyl sulfoxide or tetrahydrofuran. The conversion of the ethyl ester to a salt of structure (B) is monitored by thin layer chromatography (TLC). At this stage, depending on the compound desired, two treatments of the reaction mixture are carried out:

(a) in order to obtain the compounds of general formula (I') in which $R'_1$ is a —$CHR'_5R'_6$ radical, an alkyl halide of structure $R'_1$-X ($R'_1$=—$CHR'_5R'_6$, with $R'_5$ and $R'_6$ as defined above, X=halogen) is added to the reaction mixture comprising the salt of formula (B), the preferred halides being the chlorides or the bromides. The carboxylate anion (—$CO_2^-$) of the derivative of structure (B) displaces this halide to produce the esters of formula (Ia).

The ester thus formed is then isolated by pouring this mixture into water and by then extracting same with an organic solvent, such as a chlorinated solvent, for example dichloromethane or 1,2-dichloroethane, or an ethereal solvent, for example diethyl ether. The organic phase is separated, washed with water, then dried over sodium sulfate and, finally, concentrated. The crude ester (1a) is at this stage converted into a compound (Ib) by stirring in aqueous acidic solution (pH approximately 4), to deprotect the alcohol functional group at the 10 position. This conversion is monitored by thin layer chromatography (TLC) in order to terminate same as soon as deprotection is achieved, without the recently formed ester functional group being modified. It is also possible to carry out the deprotection of the alcohol functional group at the 10 position by treating the crude ester (Ia) with an acid resin, such as, for example, a preactivated Dowex 50W X2 resin, in an organic solvent, such as methanol, at room temperature.

(b) The compound (Ib) obtained is treated in the presence of at least 1 equivalent of a reactant, such as thionyl chloride, in order to obtain the corresponding chloride (C). This chloride is then reacted with an alkoxide of structure $R'_2$—$O^-Na^+$ ($R'^2$ having the definitions described above), following the usual conditions for displacement of a halide by an alkoxide. The compounds of general formula (I') in which $R'_1$ is a —$CHR'_5R'_6$ radical are thus obtained. This reaction yields product (Ig).

In order to obtain the compounds of formula (I') in which $R'_1$ is a hydrogen, two synthetic routes are possible:

(a') from the compounds of general formula (I') in which $R'_1$ is a —$CHR'_5R'_6$ radical which are obtained by the synthetic route described above (Ig), by saponification at a temperature of from 20° C. to 60° C. using one equivalent or an excess (2 or 3 equivalents) of an inorganic base, such as sodium hydroxide or potassium hydroxide (YOH, Y=Na or K), stirred in ethanol or in an aprotic solvent, such as dimethylformamide or dimethyl sulfoxide or tetrahydrofuran, and then stirring in aqueous acidic solution (pH approximately 4). This reaction yields product (If)

(b') an aqueous hydrochloric acid solution is added to the reaction mixture comprising the salt of 10-[(tetrahydro-2H-pyran-2-yl)oxy]-2-decenoic acid (formula B, FIGURE (I)), to a pH=1, with stirring at room temperature (20° C.), until conversion to 10-hydroxy-2-decenoic acid of formula (Ic) is complete. The reaction mixture is diluted by addition of three times its volume of water and extracted with diethyl ether or ethyl acetate. The combined organic phases are washed with water, dried over sodium sulfate and concentrated. The crude acid is subsequently purified by recrystallization from an ethyl acetate/petroleum ether mixture to result in the expected acid in the form of white crystals.

10-Hydroxy-2-decenoic acid (Ic) is treated with two equivalents of sodium ethoxide in ethanol. The dianion of structure (D) is obtained by evaporation of the solvent and is reacted in anhydrous medium in an aprotic solvent, such as dimethyl sulfoxide or tetrahydrofuran, with two equivalents of a halide of structure $R'_2$-X ($R'_2$ having the definitions described above, X=halogen) in order to obtain the compounds of general structure (Id). The compounds in which $R'_1$=H can be obtained by saponification of the compounds (Id) with 1 equivalent or a slight excess of base Y—OH, followed by acidification of the reaction mixture. The compounds of formula (I') in which $R'_1$ is a hydrogen are thus obtained.

According to the desired compound of formula (I'), when the syntheses require the use of a halide of formula $R'_1X$ or $R'_2X$ and when these $R'_1$ or $R'_2$ radicals comprise —$CO_2H$, —$CH_2OH$ or —OH groups, it may be necessary to protect the hydroxyls before reacting the $R'_1X$ or $R'_2X$ halides. This protection can be provided, for example, by a trimethylsilyl group and the —$CO_2H$, —$CH_2OH$ or —OH groups are then converted, by reaction with trimethylsilyl chloride, into ester-$CO_2Si(CH_3)_3$, ether-$CH_2$—O—$Si(CH_3)_3$ or —O—Si$(CH_3)_3$ respectively. They are then deprotected at the end of the reaction of the said $R'_1X$ or $R'_2X$ halides by hydrolysis in the presence of an acid catalyst.

In order to further illustrate the present invention and the advantages thereof, the following specific examples are given, it being understood that same are intended only as illustrative and in nowise limitative.

EXAMPLE 1

In this example, the ability of 10-hydroxy-2-decenoic acid to promote desquamation was evaluated.

This test of in vitro screening of an agent which is active with regard to desquamation was carried out on differentiated human keratinocytes. The principle of the test is based on the fact that desquamation induces the release of corneocytes. The desquamating power of the test product increases as the number of corneocytes released increases.

The protocol of the test was as follows: starting with biopsies of human skin, the keratinocytes obtained by separation from the epidermis were dissociated by enzymatic action with trypsin and were cultured at a concentration of $2\times10^5$ cell/ml. The growth and differentiation of the keratinocytes was obtained by culturing for 10 to 20 days in a specific medium. The activity of the test product was then evaluated after removal of the culture medium. To do this, two samples were taken at T0 and T60, that namely, before the addition of the product and 60 minutes after this addition. The samples thus taken were analyzed with a flow cytometer in order to count the population of corneocytes. The flow cytometer made it possible to distinguish the populations of corneocytes and of keratinocytes by treatment with acridine orange, which is specific for cellular DNA. This staining was specific for the keratinocytes, since normal corneocytes do not have nuclei and therefore do not have DNA.

The cellular detachment index was determined by the difference between T60 and T0. The same measurement was carried out for a control not comprising test product, because the experiment inevitably produced the release of corneocytes, even in the absence of active principles.

The test was carried out with 10-hydroxy-2-decenoic acid at a concentration of $5 \times 10^{-5}$ M.

The results of this study are reported in the following Table:

TABLE

| Compounds at $5 \times 10^{-5}$ M | %** |
|---|---|
| Reference* | 92 |
| 10-Hydroxy-2-decenoic acid ($R_1$ and $R_2$ = OH) | 110 |

*Reference: 2-Hydroxy-5-octanoylbenzoic acid, known to promote desquamation (FR-85/06953 assigned to the assignee hereof)
**% of activity with respect to the control composed of an identical culture in the absence of compound.
These results evidenced that the activity of 10-hydroxy-2-decenoic acid with regard to cellular detachment was high.

These results evidenced that the activity of 10-hydroxy-2-decenoic acid with regard to cellular detachment was high.

EXAMPLE 2

The following are specific examples of formulations according to the invention; these compositions were formulated by simple mixing of the various components:

| Composition 1: Milk for the face | |
|---|---|
| Liquid petrolatum | 7.0 g |
| 10-Hydroxy-2-decenoic acid | 1.0 g |
| Glyceryl monostearate, polyethylene glycol stearate (100 EO) | 3.0 g |
| Carboxyvinyl polymer | 0.4 g |
| Stearyl alcohol | 0.7 g |
| Soybean proteins | 3.0 g |
| NaOH | 0.4 g |
| Preservative | q.s. |
| Water | q.s. for 100 g |

This composition was formulated as a milk for the face having good cosmetic properties and being soft and comfortable to use.

The pH of the composition was approximately 5.5.

| Composition 2: Lotion | |
|---|---|
| Ethyl 10-(2',3'-dihydroxypropyloxy)-2-decenoate | 0.5 g |
| 2-Ethylhexyl palmitate | 10.0 g |
| Cyclopentadimethylsiloxane | 20.0 g |
| Butylene glycol | 5.0 g |
| Preservative | q.s. |
| Water | q.s. for 100 g |

This lotion, which did not contain surfactant, promoted desquamation of the skin.

| Composition 3: Milk | |
|---|---|
| Octyl palmitate | 35.0 g |
| Glycerol | 2.0 g |

| -continued | |
|---|---|
| Composition 3: Milk | |
| 1'-(Ethoxycarbonyl)ethyl 10-[1'-(ethoxycarbonyl)ethyloxy]-2-decenoate | 2.0 g |
| Acrylates/$C_{10}$–$C_{30}$ alkyl acrylates crosslinked polymer | 0.1 g |
| Triethanolamine | 0.1 g |
| Wheat amino acids | 1.0 g |
| Preservative | q.s. |
| Water | q.s. for 100 g |

The milk obtained, which did not contain surfactant, had good cosmetic properties.

| Composition 4: Gel for the face | |
|---|---|
| Glycerol | 10.0 g |
| 1'-(Ethoxycarbonyl)heptyl 10-hydroxy-2-decenoate | 2.0 g |
| Disodium cocoamphodiacetate | 1.0 g |
| Preservative | q.s. |
| Water | q.s. for 100 g |

The gel obtained had good cosmetic properties.

| Composition 5: Gel for cleansing with water | |
|---|---|
| Butylene glycol | 7.0 g |
| Sodium lauroyl sarcosinate | 4.0 g |
| Ethyl 10-(2'-hydroxybenzoyloxy)-2-decenoate | 5.0 g |
| Triethanolamine | 0.8 g |
| Carbomer | 0.5 g |
| Preservative | q.s. |
| Water | q.s. for 100 g |

The gel obtained had good cosmetic properties.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A 10-hydroxy-2-decenoic acid compound having the structural formula(I'):

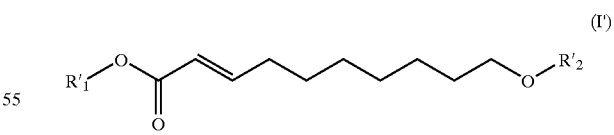

(I')

or a salt, isomer, or steroisomer thereof, in which $R'_1$ is a hydrogen atom, a radical of the formula:

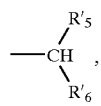

a radical of the formula:

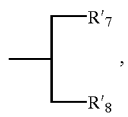

a radical of the formula:

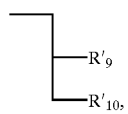

wherein $R'_5$, $R'_6$, $R'_7$, $R'_8$, $R'_9$ and $R'_{10}$ are as defined below; $R'_2$ is a hydrogen atom, a radical of the formula:

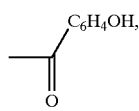

a radical of the formula:

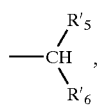

a radical of the formula:

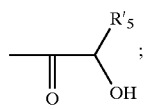

$R'_5$ is a hydrogen atom, a —$CH_3$ radical or a —$C_6H_{13}$ radical; $R'_6$ is a —COOH radical, a —$CO_2$—$CH_2$—$CH_3$ radical, a —$CH_2OH$ radical, or a hydroxyl radical; $R'_7$ is an —OH radical, a radical of the formula:

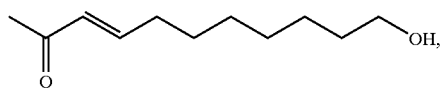

or a radical of the formula:

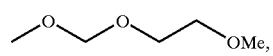

$R'_8$ is an —OH radical or a radical of the formula:

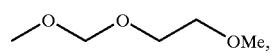

$R'_9$ is a radical of the formula:

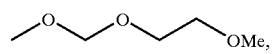

$R'_{10}$ is a radical of the formula:

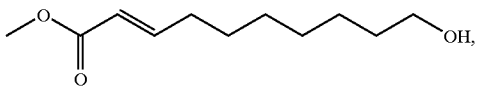

or a radical of the formula:

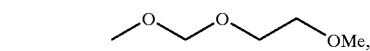

with the proviso that, when $R'_1$ is a hydrogen atom, then $R'_2$ cannot be a hydrogen atom, and that, when $R'_7$ is a radical of the formula:

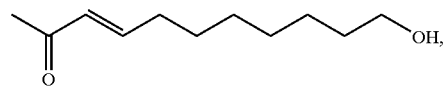

then $R'_8$ cannot be a radical of the formula:

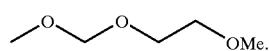

2. A method for promoting desquamation and/or stimulating epidermal renewal and/or combating intrinsic and/or extrinsic aging of the skin of an individual in need of such treatment, comprising administering thereto, for such period of time as required to elicit the desired response, a desquamation- and/or epidermal renewal- and/or skin aging combating-effective amount of at least one compound of structural formula (I'):

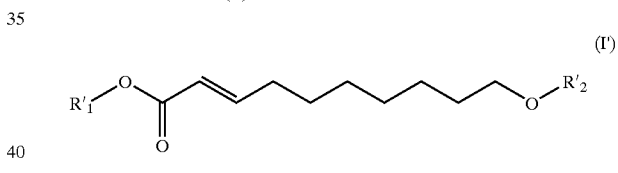

(I')

or a salt, isomer, or steroisomer thereof,
in which $R'_1$ is a hydrogen atom, a radical of the formula:

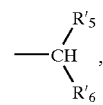

a radical of the formula:

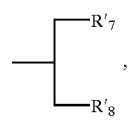

a radical of the formula:

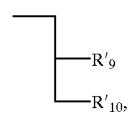

wherein $R'_5$, $R'_6$, $R'_7$, $R'_8$, $R'_9$ and $R'_{10}$ are as defined below; $R'_2$ is a hydrogen atom, a radical of the formula:

a radical of the formula:

$$-\overset{C_6H_4OH}{\underset{O}{C}}$$

a radical of the formula:

$$-CH{<}^{R'_5}_{R'_6},$$

a radical of the formula:

$$-\underset{O}{C}-\underset{OH}{C}{<}^{R'_5};$$

R'$_5$ is a hydrogen atom, a —CH$_3$ radical or a —C$_6$H$_{13}$ radical; R'$_6$ is a —COOH radical, a —CO$_2$—CH$_2$—CH$_3$ radical, a —CH$_2$OH radical, or a hydroxyl radical; R'$_7$ is an —OH radical, a radical of the formula:

[structure: CH₃-CO-CH=CH-(CH₂)₅-CH₂OH]

or a radical of the formula:

[structure: CH₃-O-CH₂-O-CH₂-CH₂-OMe]

R'$_8$ is an —OH radical or a radical of the formula:

[structure: CH₃-O-CH₂-O-CH₂-CH₂-OMe]

R'$_9$ is a radical of the formula:

[structure: CH₃-O-CH₂-O-CH₂-CH₂-OMe]

R'$_{10}$ is a radical of the formula:

[structure: CH₃-CO-CH=CH-(CH₂)₅-CH₂OH]

or a radical of the formula:

[structure: CH₃-O-CH₂-O-CH₂-CH₂-OMe]

with the proviso that, when R'$_1$ is a hydrogen atom, then R'$_2$ cannot be a hydrogen atom, and that, when R'$_7$ is a radical of the formula:

[structure: CH₃-CO-CH=CH-(CH₂)₅-CH₂OH]

then R'$_8$ cannot be a radical of the formula:

[structure: CH₃-O-CH₂-O-CH₂-CH₂-OMe]

3. The method of claim 2, wherein the salt is an alkali or alkaline earth metal salt, zinc salt, magnesium salt, strontium salt, amine salt, or quaternary ammonium salt.

4. The method as defined by claim 2, comprising administering to said individual a salt of an inorganic or organic acid of said at least one compound having the structural formula (I').

5. The method as defined by claim 4, comprising administering to said individual, an amine hydrochloride, hydrobromide or citrate of said at least one compound having the structural formula (I').

6. The method as defined by claim 2, for promoting desquamation of the skin of an individual in need of such treatment, comprising administering thereto, for such period of time as required to elicit the desired response, a desquamation-effective amount of at least one 10-hydroxy-2-decenoic acid compound having the structural formula (I').

7. The method as defined by claim 2, for stimulating renewal of the epidermal skin of an individual in need of such treatment, comprising administering thereto, for such period of time as required to elicit the desired response, an epidermal renewal-effective amount of at least one 10-hydroxy-2-decenoic acid compound having the structural formula (I').

8. The method as defined by claim 2, for combating intrinsic and for extrinsic aging of the skin of an individual in need of such treatment, comprising administering thereto, for such period of time as required to elicit the desired response, a skin aging combating-effective amount of at least one 10-hydroxy-2-decenoic acid compound having the structural formula (I').

9. A cosmetic/dermatological composition for promoting desquamation and/or stimulating epidermal renewal and/or combating intrinsic/extrinsic aging of the skin of an individual in need of such treatment, comprising an effective amount of at least one 10-hydroxy-2-decenoic acid compound have structural formula (I'), of claim 1 formulated into a cosmetically/dermatologically acceptable vehicle, diluent or carrier therefor.

10. The cosmetic/dermatological composition as defined by claim 9, wherein said cosmetically/dermatologically acceptable vehicle, diluent or carrier is topically applicable.

11. The cosmetic/dermatological composition of claim 9, wherein said at least one 10-hydroxy-2 decenoic acid compound having the structural formula (I') is from 0.001% to 20% by weight of the total weight of the composition.

12. The cosmetic/dermatological composition of claim 11, wherein said at least one 10-hydroxy-2 decenoic acid compound having the structural formula (I') is from 0.01% to 5% by weight of the total weight of the composition.

13. The cosmetic/dermatological composition of claim 9, wherein said composition is an oil-in-water emulsion.

14. The cosmetic/dermatologic composition of claim 9, wherein said composition is a water-in-oil emulsion.

15. The cosmetic/dermatologic composition of claim 9, wherein said composition is a solution, dispersion, lotion, serum, milk, suspension, gel, cream gel, cream, microcapsules, microparticles, or vesicular dispersion.

16. The cosmetic/dermatological composition of claim 9, wherein said composition is a shampoo, hair setting lotion, hair treating lotion, hair styling cream, hair styling gel, hair dyeing formulation, hair restructuring lotion, or permanent wave formulation.

17. The cosmetic/dermatological composition of claim 9, wherein said composition is an aerosol, foam, soap, capsule, granule, or tablet.

18. The cosmetic/dermatological composition of claim 9, further comprising at least one cosmetically acceptable additive or adjuvant.

19. The cosmetic/dermatological composition of claim 18, wherein said at least one additive or adjuvant comprises a hydrophilic gelling agent, lipophilic gelling agent, hydrophilic active agent, lipophilic active agent, preservative, antioxidizing agent, odor absorber, solvent, filler, fragrance, UV-screening agent, colorant, protein, protein hydrolysate, urea, amino acid, polyol, sugars, vitamin, plant extract, fatty acid, ceramide, essential oil, salicylic acids, hydroxy acid, or mixtures thereof.

20. The cosmetic/dermatological composition of claim 9, further comprising a therapeutically effective amount of at least one other active agent selected from the group consisting of a hair regrowth active agent, hair loss retarding active agent, active agent which modifies cutaneous pigmentation, active agent which modifies cutaneous proliferation, active agent which modifies cutaneous differentiation, antibacterial agent, antiparasitic agent, antifungal agent, anti-inflammatory agent, antipruriginous agent, anaesthetic, antiviral agent, keratolytic agent, anti-free-radical agent, antiacne agent, plant extract, marine extract, bacterial extract, and mixtures thereof.

21. The 10-hydroxy-2-decenoic acid compound of claim 1, wherein $R'_1$ is $CH(CH_3)(COOEt)$ and $R'_2$ is hydrogen.

22. The method of claim 2, wherein $R'_1$ is $CH(CH_3)(COOEt)$ and $R'_2$ is hydrogen.

23. The cosmetic/dermatological composition of claim 9, wherein $R'_1$ is $CH(CH_3)(COOEt)$ and $R'_2$ is hydrogen.

* * * * *